(12) United States Patent
Koenig et al.

(10) Patent No.: US 6,824,798 B2
(45) Date of Patent: Nov. 30, 2004

(54) METHOD OF PREVENTING VEISALGIA

(76) Inventors: J. Gregory Koenig, 128A Pearl Alley, Santa Cruz, CA (US) 95060; Charles Cochran, 1599 Chilton St., Arroyo Grande, CA (US) 93420

( * ) Notice: Subject to any disclaimer, the term of this patent is extended or adjusted under 35 U.S.C. 154(b) by 0 days.

(21) Appl. No.: 10/255,159

(22) Filed: Sep. 24, 2002

(65) Prior Publication Data

US 2003/0077338 A1 Apr. 24, 2003

Related U.S. Application Data

(60) Provisional application No. 60/325,877, filed on Sep. 27, 2001.

(51) Int. Cl.$^7$ .............................................. A61K 35/78
(52) U.S. Cl. ........................ 424/778; 424/725; 424/773
(58) Field of Search ................................ 424/725, 773, 424/778

(56) References Cited

FOREIGN PATENT DOCUMENTS

KR        200200695      *   1/2002

OTHER PUBLICATIONS

Product Alert. Aug. 9, 1999, vol. 29, No. 15, Newletter—Full Text PROMT Newsletter Abstract enclosed.*
Health Products Business. Dec. 2000. vol. 46, No. 12, p. 22, Full Text PROMT Newsletter Abstract enclosed.*
Website publication entitled Experts take Herbal Hangover Remedies with Grain of Salt www.intelhealth.com. May 2001 (originally provided by San Antonio Express–News). 3 pages.*
Website publication entitled "First Call—the Natural Hangover Preventative" from www.percy–french.com, downloaded from web on Jul. 2003, 2 pages.*
Weise et al. Ann. Intern. Med. 2000, vol. 132, pp. 897–902.*

* cited by examiner

Primary Examiner—Christopher R. Tate
(74) Attorney, Agent, or Firm—David Jaffer; Pillsbury Winthrop LLP

(57) ABSTRACT

A method for preventing veisalgia wherein an extract is prepared from artichoke and sarsaparilla containing a complex of polyphenols, flavonoids, and phytosterols. According to a preferred method, a dose of 1260 mg of extract is orally administered to a person prior to consuming alcohol. Subsequent to alcohol consumption another 1260 mg of extract is administered. The 1260 mg dose is adequate for most persons, is not critical, and can be scaled to a person's weight. The method as described results in complete elimination of veisalgia in more than 80% of individuals. As an alternate embodiment, the first three 420 mg quantities can be administered during consumption of alcohol. A further alternate embodiment provides an additional dose of 420 mg every hour during drinking after a period exceeding 4 hours, followed by the final dose of three 420 mg quantities at the cessation of alcohol consumption.

14 Claims, 4 Drawing Sheets

METHOD OF PREVENTING VEISALGIA

This application claims the benefit of U.S. Provisional Patent Application No. 60/325,877 filed on Sep. 27, 2001.

BACKGROUND OF THE INVENTION

1. Field of the Invention

The present invention relates generally to methods for treating veisalgia, and more particularly to a method for preventing veisalgia by administering an extract of artichoke and sarsaparilla.

2. Description of the Prior Art

Veisalgia, more commonly known as alcohol hangover has significant socio-economic consequences. According to a New York Times article of Dec. 27, 2000, referring to an article in the Jun. 6, 2000 Annals of Internal Medicine vol 132, No. 11, absenteeism and poor job performance related to alcohol hangover in the United States costs $148 billion annually. Most of this cost is associated with light to moderate drinkers (0–1 drinks per day for women, 0–3 drinks per day for men). 84% of the alcohol related problems in the workplace are caused by light to moderate drinkers. Prior art attempts to treat hangover are not very successful, and usually include consumption of pain relievers such as Acetaminophen, Ibuprofen, or aspirin which is not recommended for use in conjunction with alcohol because it can cause liver damage and gastric bleeding. Because the consumption of alcohol is known to inhibit the action of an anti-diuretic hormone on the kidneys, resulting in dehydration, attempts to minimize hangover by consuming quantities of water have been tried. Unfortunately, drinking coffee and water does little to relieve the discomfort. Although coffee may provide some short-term benefit in performance, it has a diuretic effect that perpetuates the dehydration. Even giving intravenous fluids to those suffering from a hangover resulted in only a marginal improvement. Other attempts that have failed to provide any significant relief included taking vitamin C or vitamin B, drinking fruit juice, and alternating drinks of water or juice between alcohol drinks.

In view of the above discussion, it is clear that there is a need for a method of preventing veisalgia.

SUMMARY

It is therefore an object of the present invention to provide a method of preventing veisalgia.

Briefly, a preferred embodiment of the present invention includes a method for preventing veisalgia. An extract is prepared from artichoke and sarsaparilla containing a complex of polyphenols, flavonoids, and phytosterols. According to a preferred method, a dose of 1260 mg of extract is orally administered to a person prior to consuming alcohol. Subsequent to alcohol consumption another 1260 mg of extract is administered. The 1260 mg dose is adequate for most persons, is not critical, and can be scaled to a person's weight. The method as described results in complete elimination of veisalgia in more than 80% of individuals. As an alternate embodiment, the first three 420 mg quantities can be administered during consumption of alcohol. A further alternate embodiment provides an additional dose of 420 mg every hour during drinking after a period exceeding 4 hours, followed by the final dose of three 420 mg quantities at the cessation of alcohol consumption.

IN THE DRAWING

DETAILED DESCRIPTION OF THE PREFERRED EMBODIMENT

Figure 1:
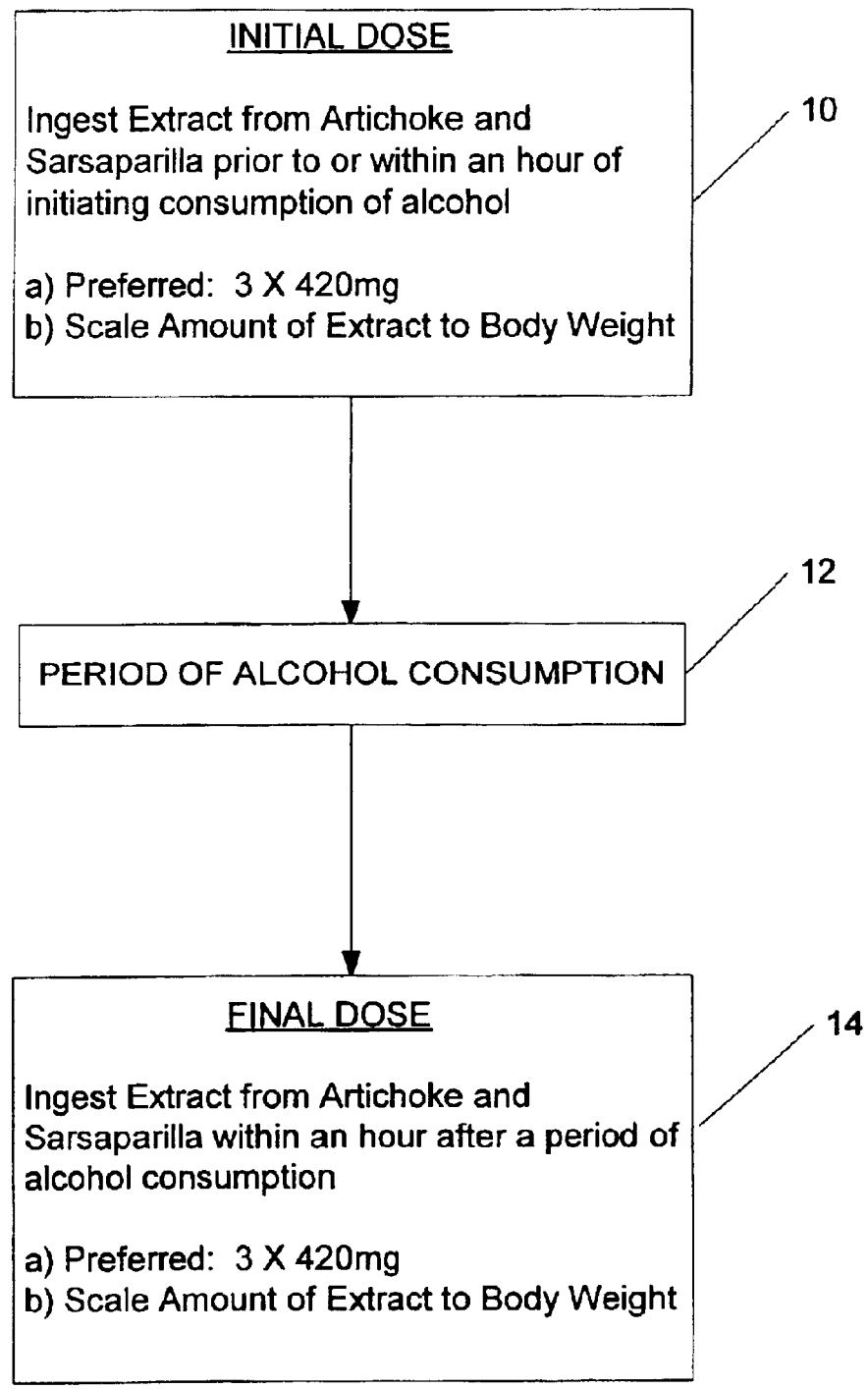
FIG. 1 is a flow chart illustrating a preferred embodiment of the method of preventing veisalgia of the present invention.
Figure 2:
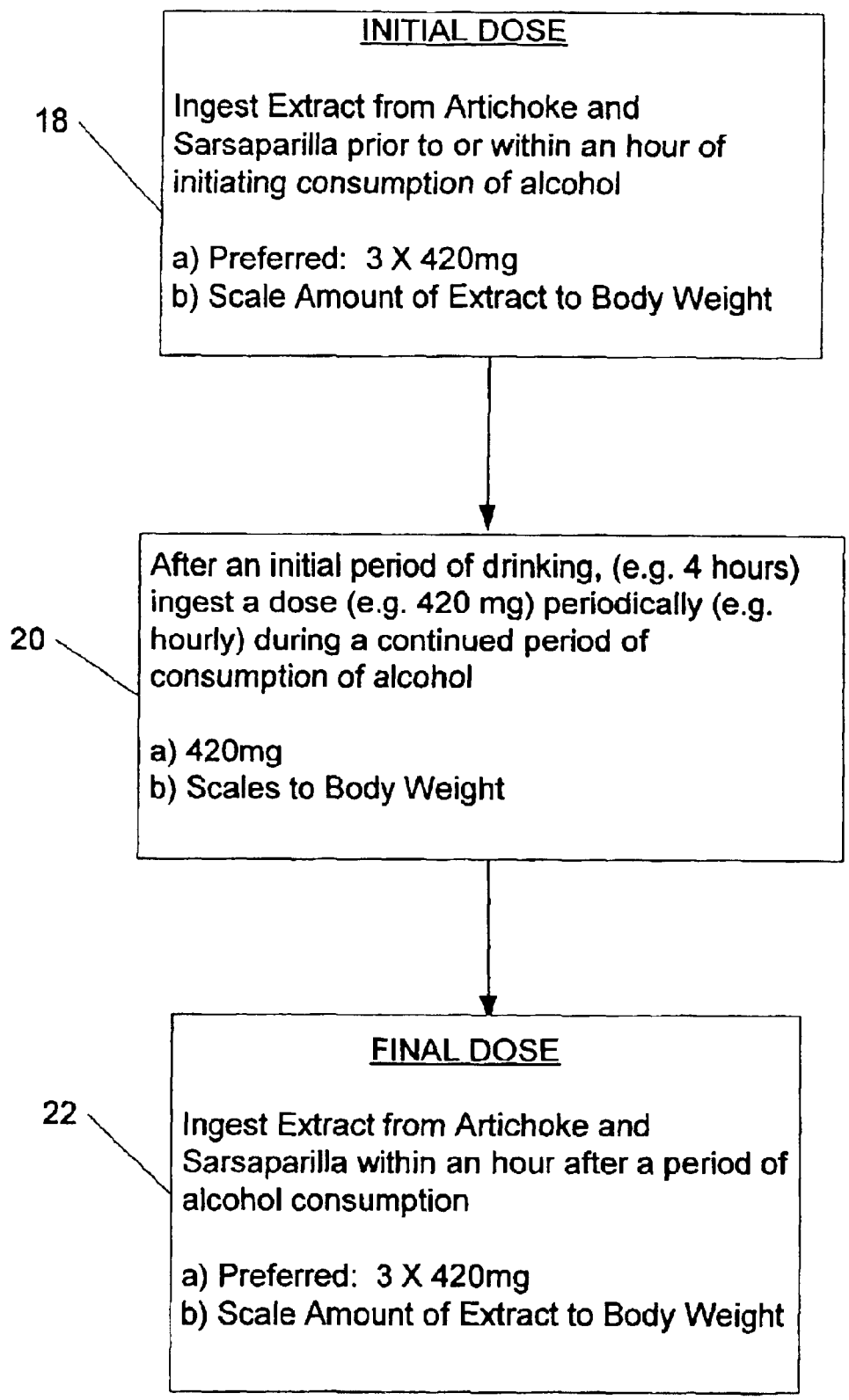
FIG. 2 is a is a flow chart illustrating an alternate embodiment of the present invention.

A preferred embodiment of the present invention is illustrated in the flow chart of FIG. 1. The method of the present invention applies generally to all levels of consumption of alcohol. The dosages prescribed in FIGS. 1 and 2 are particularly helpful in treating veisalgia resulting from moderately heavy consumption, such as 5–7 standard cocktails consumed orally over a 3–4 hour period, which almost always results in hangover symptoms. According to the method, a person ingests an initial quantity of extract of artichoke and sarsaparilla prior to or near the beginning of a period of ingesting/consuming alcohol (block 10). The quantity of extract consumed/ingested is not critical, however an amount approximate 1260 mg i.e. three 420 mg capsules is generally sufficient for most persons. A lesser amount may be sufficient for a small person, e.g. weighing 130 pounds, and a larger dose may be required for a large person weighing for example 250 pounds. An approximate amount can be determined by scaling the quantity proportional to a person's weight. The dose of extract to be taken prior to or near the beginning of a period of drinking, and again after drinking for relief from veisalgia typically ranges between 800 mg and 2000 mg, depending on various factors, including body weight. According to the method, upon consuming the extract, a person then drinks or continues to drink alcohol (block 12), and upon cessation of drinking within a relatively short period generally less than one hour, another dose of extract approximately equal to that originally ingested is consumed (block 14).

The dose of three 420 mg capsules, taken initially and again after stopping a period of drinking is sufficient to provide a satisfactory elimination of hangover for at lest 80% of users. The results can vary, depending on a person's diet, overall health, gender, weight, genetic difference in the liver, previous liver damage, and metabolism. Tests conducted to determine the effectiveness of the extract resulted in less than 3% of individuals indicating that they did not receive at least some relief from the method. Upon investigation of the persons reporting no relief, it was found that in most cases they differed significantly from the average person in some important factor. Some drank excessively i.e. greater than 10 cocktails, or consumed aspirin or other acidic product, which is also not recommended according to the method. Some had livers that were not normally effective, as evidenced by severe allergies indicating symptoms of phase I and phase II detoxification issues in the liver.

Referring now to FIG. 2, another alternate embodiment of the method of the present invention as illustrated wherein the extract is consumed periodically during a period of drinking. A dose of extract is taken prior to or early in the period of drinking, as described in reference to FIG. 1 (block 18). The method of FIG. 2 provides for extended periods of drinking, generally in excess of four hours. After an initial period of drinking, such as four hours, periodic doses of extract are consumed. Preferably the doses are taken hourly in an amount of 420 mg or approximately one-third of the initial dose. This is indicated by block 20. When the period of drinking alcohol is terminated, a final dose of extract is consumed (block 22), as described in reference to block 14 of FIG. 1. As a further alternative embodiment, instead of consuming hourly doses during extended drinking, a single larger dose, such as 840 mg to 1260 mg, taken midway in a drinking period has proven effective.

Although specific numbers have been included in the above descriptions of the various embodiments of the present invention, variations in these quantities for accomplishing the purposes set forth are also included in the spirit of the present invention. For example, an initial recommended dose is noted as ranging from 800 mg to 2000 mg depending on the person's weight and other factors. Similarly, the hourly doses during extended drinking as described in reference to block 20 of FIG. 2, and the final dose referring to block 22 of FIG. 2, have been found to be effective in the range of 420 mg to 2000 mg. Another embodiment of the present invention provides for no initial dose, and a larger final dose such as 6 capsules (2500 mg) after consumption of alcohol. Referring again to FIG. 1, for heavier drinkers, i.e. more than 7 cocktails in 3–4 hours, larger initial and final doses have been found to be useful, such as 2500 mg before drinking and 2500 mg after drinking.

Figure 3:
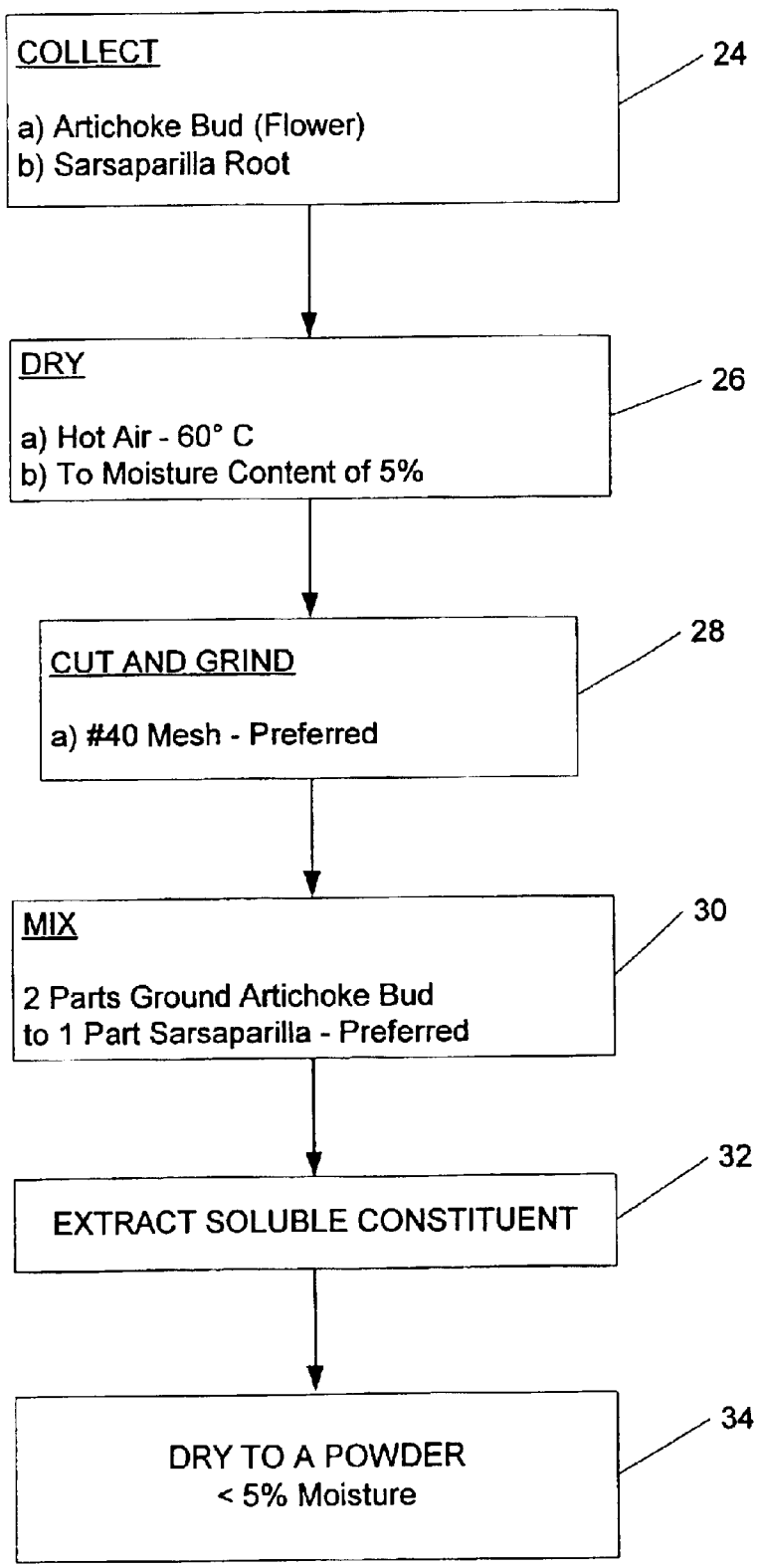
FIG. 3 is a flow chart of a method of preparing the extract for preventing veisalgia.
Figure 4:
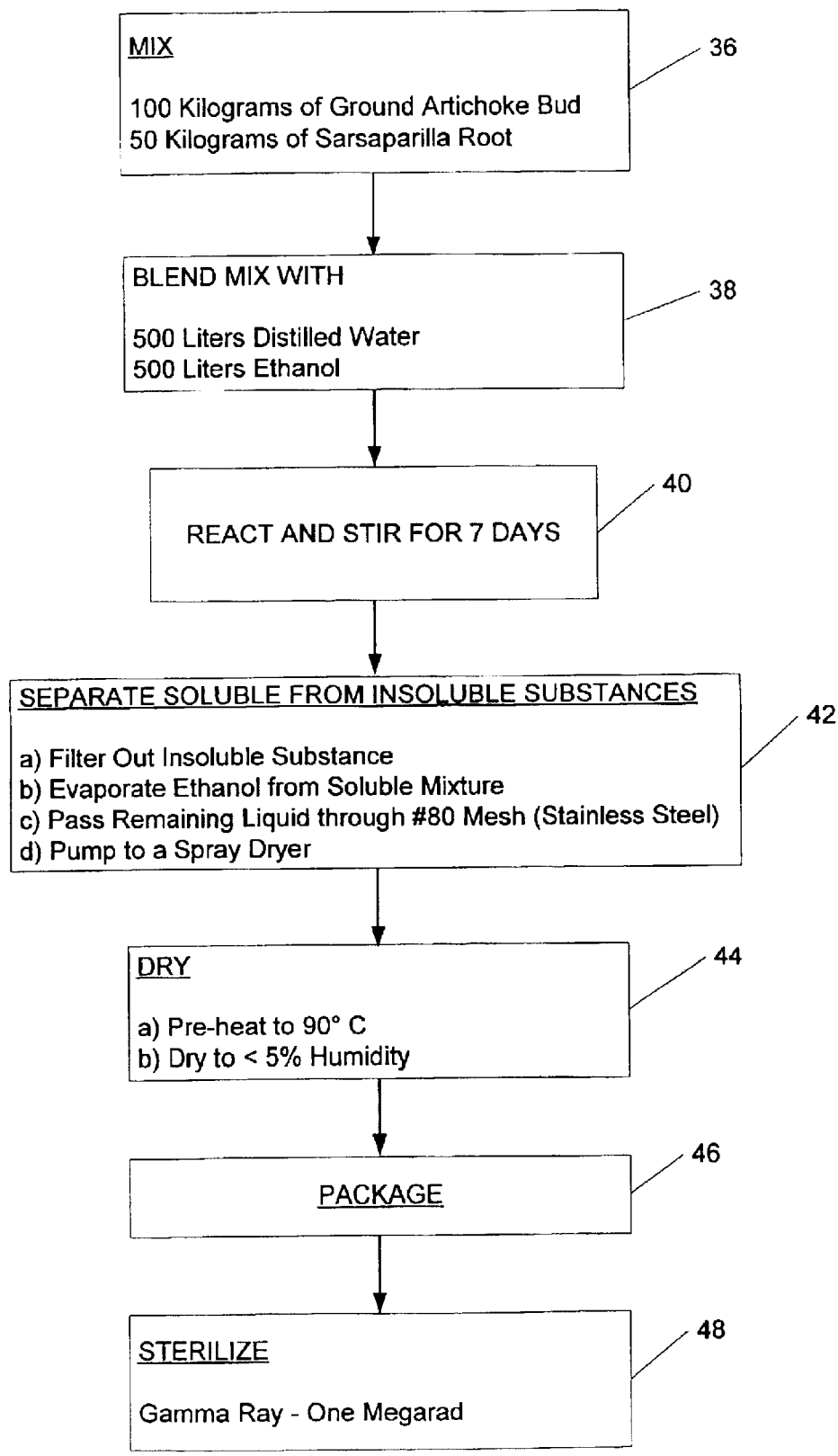
FIG. 4 provides more detail of the method of FIG. 3.

The preparation of extract will now be described in reference to FIGS. 3 and 4. The process begins with the collection of artichoke buds (flowers) and sarsaparilla root (block 24). The artichoke buds and sarsaparilla roots are then dried, preferably in hot air at 60° C. until the moisture content of these products is reduced to 5% or less (block 26). The artichoke buds and sarsaparilla roots are then each cut and ground to pass through a number 40 mesh (block 28). According to block 30, two parts of ground artichoke buds are then mixed with one part of sarsaparilla root. Following this, a soluble constituent is extracted from the mixture (block 32). The soluble constituent is then dried to a powder with less than 5% moisture content (block 34).

The processes of blocks 30, 32 and 34 will now be described in further detail along with packaging and sterilization in reference to the flow chart of FIG. 4. The mixing process of block 30 is noted in further detail in block 36 of FIG. 4 as preferably including 100 kg of ground artichoke bud with 50 kg of sarsaparilla root. Mixtures in the range of 60% to 75% by weight artichoke bud to 40% to 25% by weight sarsaparilla root are preferred. According to block 38, the mixture of block 36 is blended with 500 liters of distilled water and 500 liters of ethanol. This mixture is then allowed to react while it is being stirred for a period of 7 days (block 40). A soluble portion of the mixture resulting from block 40 is then separated from insoluble substances as indicated by block 42. This process includes first filtering out and discarding the insoluble substance, and then evaporating ethanol from the remaining soluble mixture. The remaining liquid is then passed through a number 80 mesh, preferably constructed of stainless steel. This product, extracted from the insoluble substance, is then pumped to a spray dryer. According to block 44, the substance from block 42 is dried in a dryer that is pre-heated to 90° C. The substance is then placed in the dryer until the humidity therein is less than 5%. The resultant dry product is packaged (block 46), and then subjected to a sterilization procedure, wherein the product is subjected to gamma rays in an amount equal to 1 megarad (block 48).

While particular embodiments of the present invention have been shown and described, it will be obvious to those skilled in the art that changes and modifications may be made without departing from the present invention, and therefore the claims are to encompass within their scope all such changes and modifications as follow within the true spirit and scope of the present invention.

What is claimed is:

1. A method of reducing the severity of veisalgia comprising:

(a) consuming an initial quantity of an extract prepared by extraction from artichoke buds and sarsaparilla roots in an aqueous-ethanol solution, said initial quantity being consumed prior to or during a time period of drinking alcoholic beverages; and (b) consuming a final quantity of said extract toward the end or subsequent to said time period, wherein the quantities consumed are effective to prevent veisalgia.

2. A method as recited in claim 1, wherein said initial quantity is consumed prior to said time period.

3. A method as recited in claim 1 wherein said initial quantity is consumed during said time period.

4. A method as recited in claim 1 wherein said initial quantity is in a range of 800 to 2000 mg dried weight.

5. A method as recited in claim 4 wherein said final quantity is in a range of 420 to 2000 mg dried weight.

6. A method as recited in claim 1 wherein said extract is prepared from dried and ground artichoke buds and dried and ground sarsaparilla roots.

7. A method as recited in claim 6, wherein said extract is prepared from a mixture of 60% to 75% by weight of said dried and ground artichoke buds to 40% to 25% by weight of dried and ground sarsaparilla roots.

8. A method as recited in claim 1, further comprising consuming a second quantity of said extract during said time period of drinking alcoholic beverages, and before consuming said final quantity.

9. A method as recited in claim 8 wherein said second quantity is a single dose in a range of 420 mg to 2000 mg dried weight.

10. A method as recited in claim 8 wherein said second quantity is consumed in a series of intermediate doses at periodic intervals during said time period.

11. A method as recited in claim 10 wherein consumption of said second quantity begins four hours after the beginning of said time period.

12. A method as recited in claim 10 wherein each intermediate dose is in the range of 300 to 600 mg dried weight.

13. A method as recited in claim 10 wherein said periodic interval is one hour.

14. A method as recited in claim 1 wherein said initial quantity is in a range of 800–3000 mg dried weight, and said final quantity is in a range of 800–3000 mg dried weight.

* * * * *